(12) United States Patent
Curti et al.

(10) Patent No.: US 6,439,234 B1
(45) Date of Patent: *Aug. 27, 2002

(54) NASAL CANNULA

(75) Inventors: James N. Curti; James Chua, both of Bakersfield; Peter W. Salter, Tehachapi, all of CA (US)

(73) Assignee: Salter Labs, Arvin, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/184,111

(22) Filed: Nov. 2, 1998

Related U.S. Application Data

(63) Continuation of application No. PCT/US98/05573, filed on Apr. 3, 1998.

(51) Int. Cl.$^7$ .................................................. A62B 7/00
(52) U.S. Cl. .............................. 128/207.18; 128/204.23
(58) Field of Search ........................ 128/204.18, 204.22, 128/207.18, 912, 200.24

(56) References Cited

U.S. PATENT DOCUMENTS

| 5,046,491 | A | * | 9/1991 | Derrick | 128/204.18 |
|---|---|---|---|---|---|
| 5,137,017 | A | * | 8/1992 | Salter | 128/207.18 |
| 5,335,656 | A | * | 8/1994 | Bowe et al. | 128/207.18 |
| 5,626,131 | A | * | 5/1997 | Chua et al. | 128/204.23 |
| 5,682,881 | A | * | 11/1997 | Winthrop et al. | 128/207.18 |

* cited by examiner

Primary Examiner—Glenn K. Dawson
(74) Attorney, Agent, or Firm—Davis & Bujold, P.L.L.C.

(57) ABSTRACT

An apparatus for insufflating a treating gas into a patient and for measuring a carbon dioxide content exhaled by the patient includes a hollow body with a partitioning wall separating the body into inhalation and exhalation manifolds. Two hollow prongs have coaxial openings close to the body which allow gas exchange for breathing and carbon dioxide measuring purposes. The holes are of a size such that suction drawn through the holes is limited while still allowing accurate gas analysis.

7 Claims, 1 Drawing Sheet

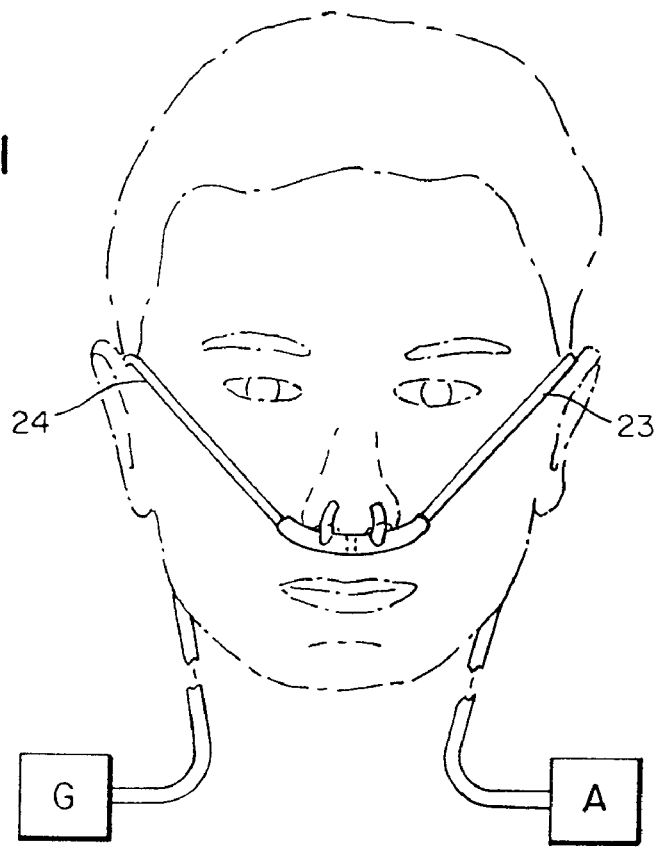
FIG. 1
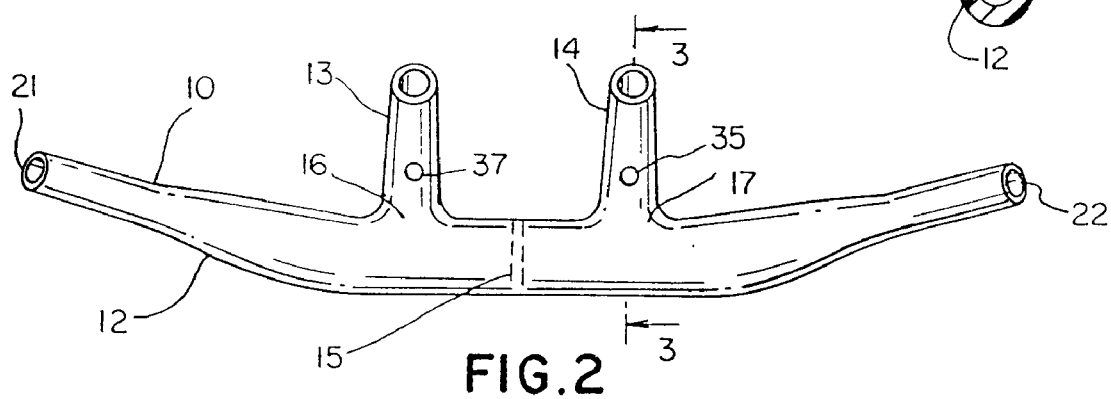
FIG. 2
FIG. 3
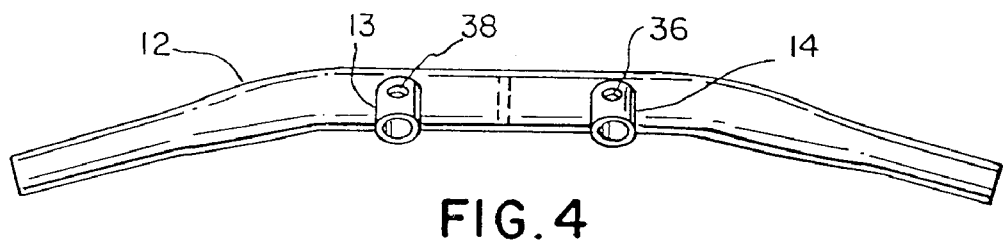
FIG. 4

NASAL CANNULA

This application is a continuation of International Application PCT/US98/05573, filed Apr. 3, 1998.

BACKGROUND OF THE INVENTION

The practice of measuring end-tidal carbon dioxide during the administration of anesthesia, particularly regional anesthesia, has grown markedly in the past several years. The reasons that anesthesiologists have embraced this technique are described more fully in U.S. Pat. No. 5,335,656 which is incorporated herein by reference in its entirety.

The preferred nasal cannula used in this procedure is a cannula which insufflates the patient with oxygen through one nare of a cannula and separately samples the exhaled gases by drawing the exhaled gas from the other nare into a conventional carbon dioxide analyzer. The cannula is preferably provided with an internal wall or system in the face piece to keep the conduits separate for insufflation and sampling, however, separate lines can be used or even multiple nares for insufflation and sampling, though the latter device substantially increases the risk of gases mixing which can distort the readings for end-tidal carbon dioxide. It is preferred that two nares only are employed and that each nare performs only one function, i.e., insufflation or sampling into or from separate nostrils. Likewise, insufflation has normally been continuous, however, it could advantageously be intermittent which would further improve the end-tidal carbon dioxide measurement by insuring that gases being sampled were representative of exhaled gases undiluted by the other gases being insufflated. Most preferably, the intermittent insufflation is accomplished by the apparatus and method described in U.S. Pat. No. 5,626,131 which is incorporated herein by reference in its entirety. Other so-called demand insufflation devices which begin insufflation upon the start of inhalation can also be employed.

Normal nasal cannulae are designed with the nares having a slight inward curvature as they extend upward from the face piece. This is anatomically desirable and important for imparting the proper direction of insufflating gas into the nasal cavities. When the patient is in the upright sitting position or ambulatory, this is the most satisfactory design configuration. Conversely, problems can be encountered if the patient is horizontal or prone and tends to accumulate secretions in the nasal cavities. It can be a particularly vexing problem if either the insufflation or sampling nare becomes occluded during the use of the cannula for sampling and monitoring end-tidal carbon dioxide during the administration of anesthesia.

OBJECTS OF THE INVENTION

It is therefore an object of the present invention to provide a nasal cannula structure for sampling carbon dioxide which reduces or eliminates the incidence of occlusion of the tip of the carbon dioxide sampling nare during the removal of carbon dioxide by the sampling line connected to a monitoring device and/or a source of suction or vacuum.

It is also an object of the present invention to provide a nasal cannula for insufflating a patient with oxygen while accurately monitoring end-tidal carbon dioxide, that will continue to function properly for its intended purpose when either or both nares become occluded for any reason.

It is a further object to accomplish the foregoing objects with a minimum risk of distorting the end-tidal carbon dioxide readings from the sampled exhalation gases during the administration of anesthesia.

BRIEF SUMMARY OF THE INVENTION

The foregoing objects and advantages are obtained by providing a nasal cannula structure that is adapted for insufflation and sampling, with additional holes or vents on the nares of the nasal cannula, preferably both anterior and posterior of one or both nares at a location proximate the entrance of the nasal passageways when the cannula is in use.

BRIEF DESCRIPTION OF THE DRAWINGS

FIG. 1 is a frontal view of a normally positioned nasal cannula on a patient (shown in phantom) connected to a gas source (G) and a gas analyzer (A).

FIG. 2 is a rear view of the cannulae face piece shown in FIG. 1.

FIG. 3 is a partial cross section of a nare of the nasal cannula taken along the lines and arrows 3—3 off FIG. 2.

FIG. 4 is a plan view of the nasal cannula of FIG. 2.

DETAILED DESCRIPTION OF THE ILLUSTRATED EMBODIMENT

The nasal cannula 10 of one embodiment of the present invention consists of a generally tubular face piece 12 having two nares 13 and 14 and a septum 15 disposed in the center of the face piece 12 between the openings 16 and 17, respectively, of the nares 13 and 14 (see FIGS. 2, 3 and 4). The openings 21 and 22 on the ends of the face piece 12 are affixed to separate tubes 23 and 24 as shown in FIG. 1, which are separately connected to a source of insufflating gas (G), such as oxygen, and a commercial carbon dioxide monitoring unit (shown as A) which, in turn, has or is connected to a vacuum pump or other means for drawing exhaled breath containing carbon dioxide into an instrument that is capable of measuring the concentration of the carbon dioxide in the sampled gas.

During use of the cannula for both insufflation and the monitoring of carbon dioxide concentration in the exhaled breath (depicted schematically in FIG. 1), the readings for end-tidal carbon dioxide can become distorted where there is undesirable mixing with room air or with excess insufflating gas. Likewise, carbon dioxide measuring devices which typically employ varying amounts of suction or vacuum to obtain the gas sample to be analyzed, can unduly dilute the sample or more seriously can draw the tip 30 of the sampling nare (representatively shown in FIG. 3) onto the adjacent surface of the tissue of the nasal passage and occlude the opening 31 thereby restricting or even preventing sampling of the exhaled gases for their carbon dioxide concentration.

This is an especially serious problem where the patient is prone and secretions can be present which are drawn into the opening 31 at the tip 30 and which then either partially or totally occlude the opening 31, during the administration of anesthesia.

The anesthesiologist must respond by clearing the nare opening after first removing the cannula from its location on the face of the patient. This may be complicated where the patient is draped in a manner which covers the cannula, such as in eye surgery. It may also be difficult to detect the occlusion where the end-tidal carbon dioxide measurement signal is only partially degraded.

It has been discovered that the expedient of additionally providing the nares with very small holes, shown collectively at 35 and 36 and 37 and 38, achieves the desired result of preventing an undesirable and unnecessary level of suction at the opening 31 of the tip 30 from developing sufficiently to draw the opening 31 into the nasal tissue thereby occluding the opening. The holes are sized large enough to prevent sufficient suction from developing at the tip 30 to draw in mucosal secretions or attach the tip by suction to the soft mucosal tissue, while still drawing an undiluted sample of the exhaled gases to provide good end-tidal carbon dioxide measurements. Likewise, too large an opening for these holes would undesirably dilute the exhaled gas sample with room air or excess insufflation gas.

Most preferably, as previously noted, the nasal cannula of the present invention can be used in combination with an oxygen delivery system that delivers the insufflating gas intermittently. The delivery can be initiated at any time after the peak end-tidal carbon dioxide measurement is achieved during exhalation and continuing into the inhalation phase of the breathing cycle or could be inhalation activated or designed to deliver only during selected portions of all or only some of the inhalation phases of a patient's breathing cycles. Preferably, the delivery should begin before the termination of the exhalation phase, such as is described in U.S. Pat. No. 5,626,131. Using intermittent delivery substantially reduces the possibility of distorted carbon dioxide readings due to gas mixing.

Likewise, slits or slots (not shown) may be employed in the nares which could function in the same manner as the holes described if they are positioned in such a manner to avoid collapse or occlusion with the nasal tissues and provide the desired function of preventing sufficient suction from developing at the tip of the nare to cause it to be drawn, by suction, onto the tissues. The holes provided as described herein are preferred as there is less risk of occlusion and trauma from the edges of slits or slots to the nasal tissue and potentially there is less risk of gas dilution and mixing from occurring where the slits or slots are overly large.

Further, the combination of intermittent insufflation using the cannula of the present invention produces the desired end-tidal carbon dioxide measurement, as described, and helps prevent patient desaturation during the rigors of surgery and anesthesia administration.

Preferably, the size of the openings is from between about 0.05 to about 0.07 inches though larger or smaller holes or single holes may be advantageously employed in combination with specific analytical apparatuses. The size and location of the openings can vary with the analyzer selected and the proper function confirmed without undue experimentation.

The invention described herein is to be limited only by the scope of the appended claims and the applicable prior art.

What is claimed is:

1. An apparatus for insufflating a treating gas into a nostril of a patient and for measuring a carbon dioxide content exhaled from a nostril of the patient, the apparatus comprising:

an elongated hollow body including a tubular portion for positioning adjacent a nose of the patient;

a partitioning wall located within the hollow body and separating the hollow body into an inhalation manifold and an exhalation manifold, the partitioning wall providing a gas-tight seal positively preventing fluid communication between the inhalation manifold and the exhalation manifold, and the inhalation manifold having a single gas entrance and the exhalation manifold having a single gas exit;

a first hollow prong having a fixed length, a first free end of the first hollow prong being opened and sized to be received with a first nasal passage of the nose for insufflating the treating gas into the nose of the patient and a second end of the first hollow prong being connected to the inhalation manifold to provide fluid communication with the single gas entrance of the inhalation manifold;

a wall of the inhalation manifold only having the single gas entrance and an opening for the attachment to the first prong and being devoid of any other openings therein;

gas supply means for connection to the single gas entrance of the inhalation manifold to supply the treating gas to the inhalation manifold and the first prong;

a second hollow prong having a fixed length, a first free end of the second hollow prong being opened and sized to be received with a second nasal passage of the nose for receiving gases exhaled from the nose of the, patient and a second end of the second hollow prong being connected to the exhalation manifold to provided fluid communication with the single gas exit of the exhalation manifold;

a pair of coaxial opposed openings provided in the second prong, and the pair of coaxial opposed openings communicate with the hollow interior of the second prong and the exhalation manifold; each opening having a diameter of between about 0.05 to 0.07 inches; and exhaled gas means for coupling to the exhalation manifold and withdrawing a gas sample exhaled from the patient via the exhalation manifold and the second prong, and carbon dioxide concentration means for coupling to the exhaled gas means and measuring a concentration of carbon dioxide in the withdrawn gas sample.

2. The apparatus according to claim 1, wherein the pair of coaxial opposed openings are axially aligned with one another and located adjacent the attachment of the second prong to the exhalation manifold.

3. The apparatus according to claim 2, wherein the first prong has a constantly tapering outer diameter which tapers from the end attached to the elongate hollow body to the free end of the first prong, and the second prong has a constantly tapering outer diameter which tapers from the end attached to the elongate hollow body to the free end of the second prong.

4. The apparatus according to claim 2, wherein said first prong has a pair of opposed openings, each of the pair of opposed openings in the first prong and the second prong have a diameter of between about 0.05 to 0.07 inches.

5. An apparatus for insufflating a treating gas into a nostril of a patient and for measuring a carbon dioxide content exhaled from a nostril of the patient, the apparatus comprising:

an elongated hollow body including a tubular portion for positioning adjacent a nose of the patient;

a partitioning wall located within the hollow body and separating the hollow body into an inhalation manifold and an exhalation manifold, the partitioning wall providing a gas-tight seal positively preventing fluid communication between the inhalation manifold and the exhalation manifold, and the inhalation manifold having a single gas entrance and the exhalation manifold having a single gas exit;

a first hollow prong having a fixed length, a first free end of the first hollow prong being opened and sized to be received with a first nasal passage of the nose for insufflating the treating gas into the nose of the patient and a second end of the first hollow prong being connected to the inhalation manifold to provide fluid communication with the single gas entrance of the inhalation manifold;

a pair of coaxial opposed openings provided in the first prong, the pair of coaxial opposed openings of the first prong both being located closer to the elongate hollow body than the open end of the first prong to communicate directly with the hollow interior of the first prong and the inhalation manifold;

a wall of the inhalation manifold only having the single gas entrance and an opening for the attachment to the first prong but being devoid of any other openings therein;

gas supply means connected to the single gas entrance of the inhalation manifold to supply the treating gas to the inhalation manifold and the first prong;

a second hollow prong having a fixed length, a first free end of the second hollow prong being opened and sized to be received with a second nasal passage of the nose for receiving gases exhaled from the nose of the patient and a second end of the second hollow prong being connected to the exhalation manifold to provide fluid communication with the single gas exit of the exhalation manifold;

a pair of coaxial opposed openings provided in the second prong, the pair of coaxial opposed openings of the second prong both being located closer to the elongate hollow body than the open end of the second prong to communicate directly with the hollow interior of the second prong and the exhalation manifold; wherein each of the opposed openings has a diameter of about 0.05 to 0.07 inches;

a wall of the exhalation manifold only having the single gas exit and an opening for the attachment to the second prong but being devoid of any other openings therein; and exhaled gas means, coupled to the exhalation manifold, for withdrawing a gas sample exhaled from the patient via the exhalation manifold and the second prong, and carbon dioxide concentration means, coupled to the exhaled gas means, for measuring a concentration of carbon dioxide in the withdrawn gas sample.

6. The apparatus according to claim 5, wherein the first prong has a constantly tapering outer diameter which tapers from the end attached to the elongate hollow body to the free end of the first prong, and the second prong has a constantly tapering outer diameter which tapers from the end attached to the elongate hollow body to the free end of the second prong.

7. An apparatus for insufflating a treating gas into a nostril of a patient and for measuring a carbon dioxide content exhaled from a nostril of the patient, the apparatus consisting of:

an elongated hollow body including a tubular portion for positioning adjacent a nose of the patient;

a partitioning wall located within the hollow body and separating the hollow body into an inhalation manifold and an exhalation manifold, the partitioning wall providing a gas-tight seal positively preventing fluid communication between the inhalation manifold and the exhalation manifold, and the inhalation manifold having a single gas entrance and the exhalation manifold having a single gas exit;

a first hollow prong having a fixed length, a first free end of the first hollow prong being opened and sized to be received with a first nasal passage of the nose for insufflating the treating gas into the nose of the patient and a second end of the first hollow prong being connected to the inhalation manifold to provided fluid communication with the single gas entrance of the inhalation manifold; and the first prong having a constantly tapering outer diameter which tapers from the end attached to the elongate hollow body to the free end of the first prong;

a pair of coaxial opposed openings provided in the first prong, the pair of coaxial opposed openings of the first prong both being located adjacent the elongate hollow body, in a wider diameter tapered portion of the first prong, and spaced from the open end of the first prong to communicate directly with the hollow interior of the first prong and the inhalation manifold;

a wall of the inhalation manifold only having the single gas entrance and an opening for the attachment to the first prong but being devoid of any other openings therein;

gas supply means connected to the single gas entrance of the inhalation manifold to supply the treating gas to the inhalation manifold and the first prong;

a second hollow prong having a fixed length, a first free end of the second hollow prong being opened and sized to be received with a second nasal passage of the nose for receiving gases exhaled from the nose of the patient and a second end of the second hollow prong being connected to the exhalation manifold to provide fluid communication with the single gas exit of the exhalation manifold; and the second prong having a constantly tapering outer diameter which tapers from the end attached to the elongate hollow body to the free end of the second prong;

a pair of coaxial opposed openings provided in the second prong, the pair of coaxial opposed openings of the second prong both being located adjacent the elongate hollow body, in a wider diameter tapered portion of the second prong, and spaced from the open end of the second prong to communicate directly with the hollow interior of the second prong and the exhalation manifold;

a wall of the exhalation manifold only having the single gas exit and an opening for the attachment to the second prong but being devoid of any other openings therein; and exhaled gas means, coupled to the exhalation manifold, for withdrawing a gas sample exhaled from the patient via the exhalation manifold and the second prong, and carbon dioxide concentration means, coupled to the exhaled gas means, for measuring a concentration of carbon dioxide in the withdrawn gas sample; and each of the pair of coaxially opposed openings in the first prong and the second prong having a diameter of between about 0.05 to 0.07 inches.

* * * * *